(12) United States Patent
Yang et al.

(10) Patent No.: US 8,298,328 B2
(45) Date of Patent: Oct. 30, 2012

(54) AMORPHOUS METAL SALT FOR FACILITATING THE HANDLING PROPERTY OF PORTLAND CEMENTS AND DENTAL APPLICATIONS THEREOF

(75) Inventors: Jeng-Chang Yang, Taipei (TW); Pei-Ying Lee, Taipei (TW); Dian-Yu Ji, Taipei (TW); Nai-Chia Teng, Taipei (TW); Sung-Chih Hsieh, Sindian (TW); Sheng-Yang Lee, Taipei (TW)

(73) Assignee: Taipei Medical University, Taipei (TW)

( * ) Notice: Subject to any disclaimer, the term of this patent is extended or adjusted under 35 U.S.C. 154(b) by 307 days.

(21) Appl. No.: 12/591,764

(22) Filed: Dec. 1, 2009

(65) Prior Publication Data

US 2010/0139524 A1    Jun. 10, 2010

(30) Foreign Application Priority Data

Dec. 10, 2008 (TW) ................................ 97147977 A

(51) Int. Cl.
*A61K 6/06* (2006.01)
(52) U.S. Cl. .......... 106/35; 106/724; 106/725; 106/727; 106/728; 106/734; 106/736; 106/801; 106/802; 433/228.1; 433/224
(58) Field of Classification Search ............... 433/228.1, 433/224; 423/311, 395, 497, 554, 559; 106/35, 106/724, 725, 727, 728, 734, 736, 801, 802
See application file for complete search history.

(56) References Cited

U.S. PATENT DOCUMENTS 5,531,983 A * 7/1996 Van Velthuijsen .............. 424/49
(Continued)

FOREIGN PATENT DOCUMENTS

WO    WO 99/65337    * 12/1999
(Continued)

OTHER PUBLICATIONS

Kenneth B. Wiltbank, et al. Effect of Selected Accelerants on the Physical Properties of Mineral Trioxide Aggregate and Portland Cement; Journal of Endodontics, Oct. 2007; vol. 33; p. 1235-1238; The American Association of Endodontists.

(Continued)

*Primary Examiner* — Carol M Koslow
(74) *Attorney, Agent, or Firm* — Bacon & Thomas, PLLC

(57) ABSTRACT

A novel amorphous divalent metal ion salt for enhancing the manageability of a Portland cement and its application in dental field are disclosed. Typical formula (I), (II), or (III) of this amorphous metal ion salt are shown as following:

$$M^{2+}A^-_x B^-_{2-x} \qquad (I)$$

$$M^{2+}A^-_{\frac{y}{2}} C^{2-}_{\frac{(4-y)}{4}} \qquad (II)$$

$$M^{2+}A^-_{\frac{z}{3}} D^{3-}_{\frac{(6-z)}{9}} \qquad (III)$$

wherein, $M^{2+}$, $A^-$, $B^-$, $C^{2-}$, $D^{3-}$, x, y, and z are defined the same as the specification. A novel tooth filling material comprises: a Portland cement, a bone substitute substance, and an amorphous divalent metal ion salt with formula of (I), (II), or (III). In addition, a novel root canal filling material comprises: a Portland cement, a radiopaque substance, and an amorphous divalent metal ion salt with formula of (I), (II), or (III). This amorphous divalent metal ion salt in the filling material of the present invention can improve the sticking together and reduce the setting time, thus offering more convenient in dental applications.

16 Claims, 2 Drawing Sheets

U.S. PATENT DOCUMENTS

| | | | |
|---|---|---|---|
| 5,554,218 A | 9/1996 | Evans et al. | |
| 5,605,571 A | 2/1997 | Buerge et al. | |
| 5,792,252 A | 8/1998 | Sprouts | |
| 6,106,874 A * | 8/2000 | Liebrecht et al. | 426/74 |
| 6,576,277 B2 * | 6/2003 | Livisay et al. | 426/74 |
| 7,294,187 B2 | 11/2007 | Chow et al. | |
| 2002/0065317 A1 * | 5/2002 | Dizer et al. | 514/557 |
| 2006/0263443 A1 | 11/2006 | Chow et al. | |
| 2007/0009858 A1 | 1/2007 | Hatton et al. | |
| 2007/0082118 A1 * | 4/2007 | Fletcher | 426/656 |

FOREIGN PATENT DOCUMENTS

| | | |
|---|---|---|
| WO | 2005039509 A1 | 5/2005 |
| WO | 2008102214 A2 | 8/2008 |

OTHER PUBLICATIONS

Seung-Jong Lee, et al, Sealing Ability of a Mineral Trioxide Aggregate for Repair of Lateral Root Perforations; Journal of Endodontics, Nov. 1993; vol. 19; p. 541-544; The American Association of Endodontists.

Shinn Jyn Ding, et al. The Physical Cytological Properties of White MTA Mixed with Na2HPO4 as an Accelerant; Journal of Endodontics, Jun. 2008; vol. 34; p. 748-751; The American Association of Endodontists.

* cited by examiner

AMORPHOUS METAL SALT FOR FACILITATING THE HANDLING PROPERTY OF PORTLAND CEMENTS AND DENTAL APPLICATIONS THEREOF

BACKGROUND OF THE INVENTION

1. Field of the Invention

The present invention relates to a novel amorphous divalent metal salt to shorten the setting time and improve the handling property for the Portland cements. A powder mixture consisting of hydrophilic particles including Portland cement clinker, bismuth oxide, and gypsum is extensively applied as a dental filling material. Therefore, the hydration of this dental filling material should undergo similar mechanisms as Portland cement. The endodontic applications of the amorphous metal salt illustrated below are also related. The amorphous metal salt consisting of a divalent metal ion and two independent and different organic and/or inorganic acid anions has high solubility by way of disturbing the regularity of the atomic arrangement. Furthermore, at the end of the hydration of the Portland cements, the amorphous metal salt can separate out to enhance the viscosity. It can reduce the setting time and improve the sticking together properties of Portland cements. Hence, the amorphous metal salt of the present invention can enhance the manageability of the Portland cements as well as the dental filling materials for clinic applications.

2. Description of Related Art

According to ASTM International Standard C150, Portland cements are classified into five types according to the various contents of compositions in the cements. Type I Portland cement is known as common cement; Type II Portland cement has moderate sulfate resistance and moderate heat of hydration; Type III Portland cement has relatively high early strength; Type IV Portland cement has low heat of hydration; and Type V Portland cement has sulfate resistance.

Typical type I Portland cement consists of 50% of tricalcium silicate ($3CaO.SiO_2$), 25% of dicalcium silicate ($2CaO.SiO_2$), 10% of tricalcium aluminate ($3CaO.Al_2O_3$), 10% of tetracalcium aluminoferrite ($4CaO.Al_2O_3.Fe_2O_3$), and 5% of calcium sulfate dehydrate ($CaSO_4$, gypsum). When Portland cement powder is mixed with water, hydration reaction starts and cement hardens. The major chemical equation is represented as follows.

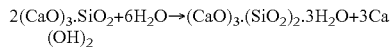

$2(CaO)_3.SiO_2+6H_2O \rightarrow (CaO)_3.(SiO_2)_2.3H_2O+3Ca(OH)_2$

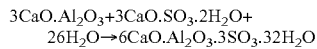

$3CaO.Al_2O_3+3CaO.SO_3.2H_2O+26H_2O \rightarrow 6CaO.Al_2O_3.3SO_3.32H_2O$

As shown in the aforementioned chemical equation, water and $Ca^{2+}$ involves in the hydration reaction of Portland cement. The ratio of water to cement powder influences the dispersion of each components in Portland cement, and also relates to the forming rate of calcium silicate hydrates (C—S—H) and calcium aluminate hydrates (C-A-H), and the physical properties of hard cement.

Additives for regulating the hydration rate have been extensively investigated to improve the workability as well as the handling properties of Portland cement. It is believed that organic compounds with many $OH^-$ groups act as good retarders due to adsorption by hydrogen bonding. The retarding action on cement by poisoning the hydrate nuclei or by blocking the water molecules is further classified in terms of four different theories, namely, precipitation, nucleation, complexation, and adsorption. In the cement literature, the hydration retarders include various metal gluconates, dextrins, high dose (0.2~0.4 wt %) citric acid, α-hydroxy carboxylic acids, sucrose, and calcium sulfate. On the other hand, C—S—H gel and calcium hydroxide evolve by crystallization after hydration reaction. An additive-mediated nucleation and growth mechanism governs the crystallization process and results in accelerating the setting reaction. Typical accelerators include glucose, low dose (0.1 wt %) citric acid, lactic acid, calcium formate, and calcium chloride.

Currently, rapid hardening cement is developed to meet the requirement of short setting time. The rapid hardening cement can be manufactured by sintering limestone and bauxite to produce cement clinker, followed by finely grinding the cement clinker into powder. Alternatively, the rapid hardening cement can be manufactured by adding additive into Portland cement to accelerate the hardening process after the hydration reaction of the Portland cement. In 1996, U.S. Pat. No. 5,554,218 disclosed that the hydration reaction can be accelerated by adding $CaCl_2$ with diameters of 2,250 μm or less into Portland cement to shorten the setting time. In addition, U.S. Pat. No. 5,792,252 disclosed that alkali metal carbonate is added into the cement to accelerate cement hardening process, and the initial setting time of cement can be reduced to 35~145 min.

U.S. Pat. No. 5,605,571 disclosed an additive without chloride and nitrite, which comprises 1~35% of alkanolamine, 1~20% of thiocyanate, 1~25% of carboxylic acid, and 1~40% of a component comprising nitrate, sulfite, or a combination thereof. The initial setting time of Portland cement can be shortened to 120~150 min by adding the additive illustrated above into the Portland cement.

In clinic, the inflamed tissues are in an acidic environment, which has a pH value reduced from 7.35 of the normal tissues to 5.6. The hydrated Portland cement has high alkalinity (about pH 12) and is a fine solid filling structure, which is a suitable biomaterial, and can be used as a dental material to seal the roots and ease symptoms of inflammation. However, the clinical use and need for Portland cement are different from those for the architecture. Therefore, there is a necessity for developing a product using Portland cement, which can meet the demands for clinical use.

In clinic, tooth cavities and root canal fillings are common dental problems. Endodontic treatment is a method, which treats diseased pulps and root ends by pulp capping, pulpotomy, or root filling to seal the affected parts. That can prevent inflammation cased by bacteria infection, and heal the tissues around the roots. In dental clinic, there are various kinds of filling materials used in endodontic treatment. Among these materials, most of them are tried to seal the root canals and the root ends, or fill the canals between periodontal tissues. The examples of the filling materials are amalgam, gutta percha, Cavit, IRM, Super EBA, composite resin, and glass ionomer cement. However, the aforementioned filling materials have problems in microleakage, cytotoxicity, poor handling property, and moisture sensitivity. Hence, these materials are not ideal filling materials for retrograde filling or perforation repairing.

Ideal filling materials should have the characteristics of good filling property, good biocompatibility, and simple clinical handling. Also, ideal filling materials should meet the demands for stable volume, undissolvable property, no interaction with tissue fluid, and also have the character of radiopacity.

Among the dental filling materials used in the endodontic treatment, mineral trioxide aggregate (MTA) developed by Dentsply Co. has the properties of high alkalinity, good sealing property, margin sealing, biocompatibility, and inducing cytokine release. The MTA can be widely used in the endodontic treatment, such as the root-end filling, repair of root and furcation perforation, pulp capping, pulpotomy, and apexification.

Mineral trioxide aggregate, called MTA, is an aggregate of mineral oxides for sealing roots and root-ends, or filling canals between periodontal tissues by Lee et al. at Loma Linda University in 1993. The main component of MTA is tricalcium complex powder comprising calcium oxide and calcium silicate. The mineral oxides add to adjust the chemical and physical properties of MTA. The first developed MTA is grey MTA, and the main components are 75 wt % of type I Portland cement, 5 wt % of gypsum, and 20 wt % of bismuth oxide. However, the set grey MTA has a grey green hue, which influences the appearance of repaired tooth color. Hence, Dentsplay Co. has developed novel white MTA to replace the grey MTA. In the white MTA, the tetra-calcium aluminoferrite with deep green color is removed from Portland cement. In addition, bismuth oxide has x-ray radiopacity property. Hence, when the white MTA is used to seal roots and root-ends, the irradiation method can be used to detect the filling condition.

Although MTA has excellent filling effect, the setting time of MTA is about 3 to 4 hours. The setting time is too long, the tissue fluid or blood may cause the MTA to be washed away during the operation, which influences the sealing property and treating effect. Furthermore, the powders of the MTA are in granular form at the initial stage of blending and hard to aggregate.

In order to solve the aforementioned problems, WO 2005/039509A1 provides a dental filling material having Portland cement (i.e. the main component of MTA) as a major component, and the handling property is enhanced by adding poly(vinyl alcohol) as a viscosity enhancing substance. However, this dental filling material cannot reduce the initial setting time of Portland cement. In addition, the radiopaque substance contained in the dental filling material is bismuth oxide, so the problem of the unnatural tooth color is still unsolved.

In addition, U.S. Pat. No. 2007009858 discloses a dental filling material, which comprises $CaCl_2$ as a hardening accelerator, and cellulose as a thickening agent, in order to improve the long initial setting time and poor handling properties of MTA. The setting time of the dental filling material can be reduced to 35 min by adding $CaCl_2$ and cellulose. However, the particle size of $CaCl_2$ is somewhat large (250~1,250 μm), which causes the powders of MTA hard to be aggregated after blending MTA.

In 2007, Wiltbank et al. disclosed that the setting time of MTA can be shortened from 3~4 hr to 35~45 min by adding 5 wt % $CaCl_2$, and the pH value of set MTA is about 11~12. In addition, the setting time of MTA can be shortened to 15 min by adding 5 wt % calcium formate, and the pH value of set MTA is about 13. However, the problem of poor handling property when blending MTA is still unsolved.

In addition, in 2008, Ding et al. disclosed that the setting time of white MTA can be shortened to 25 min by adding $Na_2HPO_4$. However, $Na_2HPO_4$ can only help to accelerate initial hydration reaction, but cannot facilitate the handling property during blending MTA.

The ideal setting time is 10~15 min. Calcium compound or $Na_2HPO_4$ can be used as a hydration accelerator to shorten the initial setting time to about 40 min is still not achieved clinical requirement. Furthermore, these methods cannot facilitate the handling property during blending MTA. Hence, if a material can combine the hydration hardening accelerator and the thickening agent, the material for treatment of endodontic can be simplified the formula and the certification of medical devices. Therefore, it is desirable to develop an additive, which can reduce the setting time of MTA hydration and facilitate the handling property at the same time.

SUMMARY OF THE INVENTION

The object of the present invention is to provide an amorphous divalent metal salt, which can reduce the setting time and improve the aggregation when mixed with Portland cement. Hence, Portland cement can improve its handling property.

To achieve the object, the amorphous divalent metal salt for facilitating the handling property of a Portland cement of the present invention is represented by the following formulas (I), (II), or (III):

$$M^{2+}A_x^- B_{2-x}^- \tag{I}$$

$$M^{2+}A_{\frac{y}{2}}^- C_{\frac{(4-y)}{4}}^{2-} \tag{II}$$

$$M^{2+}A_{\frac{z}{3}}^- D_{\frac{(6-z)}{9}}^{3-} \tag{III}$$

wherein, $M^{2+}$ is a metal ion. $A^-$, $B^-$, $C^{2-}$, $D^{3-}$ are independently and different from each other which is $C_1$~$C_{15}$ organic or inorganic acid anions. $0<x<2$, $0<y<4$, and $0<z<6$. Herein, facilitation of the handling property means short setting time and improvement in the aggregation of blending with Portland cement.

Another object of the present invention is to provide a novel solution of an amorphous divalent metal salt, which can be used in a dental material with short setting time and good clinical handling property for repairing tooth cavities or root canal filling.

To achieve the object, the dental material for repairing tooth cavities of the present invention comprises: a powder composition and a solution of an amorphous divalent metal salt. Herein, the powder composition comprises a Portland cement, a calcium phosphate bone substitute, and further comprises gypsum selectively. The amorphous divalent metal salt is represented by the following formulas (I), (II), or (III):

$$M^{2+}A_x^- B_{2-x}^- \tag{I}$$

$$M^{2+}A_{\frac{y}{2}}^- C_{\frac{(4-y)}{4}}^{2-} \tag{II}$$

$$M^{2+}A_{\frac{z}{3}}^- D_{\frac{(6-z)}{9}}^{3-} \tag{III}$$

wherein, $M^{2+}$ is a metal ion. $A^-$, $B^-$, $C^{2-}$, $D^{3-}$ are independently and different from each other which is $C_1$~$C_{15}$ organic or inorganic acid anions. $0<x<2$, $0<y<4$, and $0<z<6$. In addition, the calcium phosphate bone substitute is β-tricalcium phosphate (β-TCP), or amorphous calcium phosphate (ACP).

Furthermore, the present invention also provides a dental material for root canal filling, which comprises: a powder composition and a solution of an amorphous divalent metal salt. Herein, the powder composition comprises a Portland cement, a radiopaque substance, and further comprises gyp sum selectively. The amorphous divalent metal salt is represented by the following formulas (I), (II), or (III):

$$M^{2+}A^-_x B^-_{2-x} \quad \text{(I)}$$

$$M^{2+}A^-_{\frac{y}{2}} C^{2-}_{\frac{(4-y)}{4}} \quad \text{(II)}$$

$$M^{2+}A^-_{\frac{z}{3}} D^{3-}_{\frac{(6-z)}{9}} \quad \text{(III)}$$

wherein, $M^{2+}$ is a metal ion. $A^-$, $B^-$, $C^{2-}$, $D^{3-}$ are independently and different from each other which is $C_1\sim C_{15}$ organic or inorganic acid anions. $0<x<2$, $0<y<4$, and $0<z<6$. In addition, the radiopaque substance is bismuth subcarbonate, or bismuth oxide.

In the amorphous divalent metal salt, repairing tooth cavities materials, and root canal filling materials of the present invention with cement, is preferably type I Portland cement. However, other types of Portland cement can also be used in the present invention. The type I Portland cement comprises the following components:

| Component | Percentage (%) |
|---|---|
| $SiO_2$ | 18~23 |
| $Al_2O_3$ | 2~6 |
| $Fe_2O_3$ | 3~7 |
| CaO | 62~68 |
| MgO | 0.5~4 |
| $SO_3$ | 1~4 |
| Alkali metal oxide ($Na_2O$, $K_2O$) | 0~2 |

In the amorphous divalent metal salt, the dental material for repairing tooth cavities, and the dental material for root canal filling of the present invention, the Blaine number of Portland cement can be in a range of 4,000 to 5,500 cm²/g. Preferably, the Blaine number is in a range of 4,600 to 5,500 cm²/g.

In the amorphous divalent metal salt, repairing tooth cavities materials, and root canal filling materials of the present invention, $M^{2+}$ can be a metal ion of group IIA. Preferably, $M^{2+}$ is selected from the group consisting of $Be^{2+}$, $Mg^{2+}$, $Ca^{2+}$, $Sr^{2+}$, and $Ba^{2+}$. More preferably, $M^{2+}$ is $Ca^{2+}$.

In the amorphous divalent metal salt, repairing tooth cavities materials, and root canal filling materials of the present invention, the inorganic acid anions are containing N, P, S, or halogen ion. Preferably, the inorganic acid ion is selected from the group consisting of nitrate, sulfate, chloride, and phosphate.

In the amorphous divalent metal salt, repairing tooth cavities materials, and root canal filling materials of the present invention, the organic acid anions are selected from the group consisting of gluconate, lactate, pyruvate, glycolate, chloractate, dichloroacetate, trichloroacetate, cyanoacetate, tartrate, succinate, glutarate, maleate, fumarate, malonate, citraconate, ortho-phthalate, meta-phthalate, para-phthalic, citrate, 1,2,3-propanetricarboxylate, trimellitate, and 1,3,5-pentanetricarboxylate.

In the amorphous divalent metal salt, repairing tooth cavities materials, and root canal filling materials of the present invention, preferably, $A^-$ is lactate, and $B^-$ is gluconate in formula (I).

In the amorphous divalent metal salt, repairing tooth cavities materials, and root canal filling materials of the present invention, the amorphous divalent metal salt can be calcium lactate gluconate (CLG), calcium lactate sulfate (CLS), or calcium sulfate gluconate (CSG). Preferably, the amorphous divalent metal salt is calcium lactate gluconate (CLG).

In the amorphous divalent metal salt, repairing tooth cavities materials, and root canal filling materials of the present invention, the solution of the amorphous divalent metal salt is at a concentration of between 5% and 30% by weight, the liquid-to-powder ratio (L/P ratio) of the solution of the amorphous divalent metal salt to the powder composition is between 1:2 and 1:5. Furthermore, the content of the radiopaque substance is in a range of 10 to 25% by weight.

When the dental material of the present invention is used for repairing tooth, the tooth cavities and root canals can be sealed by the hydration reaction of the Portland cement contained dental filling materials. The hydration reaction of Portland cement depends on water and $Ca^{2+}$. Although calcium-containing compound can enhance the hydration of Portland cement in initial setting reaction, the crystallized precipitates formed from saturated calcium-containing compound cannot facilitate the handling property. In the present invention, a solution of an amorphous divalent metal salt is used to enhance the reaction rate of the Portland cement hydration, and the saturated precipitates can improve the aggregation of the dental materials. Hence, the amorphous divalent metal salt of the present invention can enhance the clinical handling property. Furthermore, according to the root canal filling material of the present invention, bismuth subcarbonate is used to replace bismuth oxide, so the problem of the dark color can be solved in repaired tooth.

In addition, the present invention further provides a method for preparing a dental material for repairing tooth cavities or root canal filling, which comprises the following steps: (A) providing the aforementioned powder composition, and the solution of the amorphous divalent metal salt; and (B) mixing the powder composition with the solution of the amorphous divalent metal salt.

In the method of the present invention, the L/P ratio of the solution of the amorphous divalent metal salt to the powder composition is between 1:2 and 1:5.

Other objects, advantages, and novel features of the invention will become more apparent from the following detailed description when taken in conjunction with the accompanying drawings.

DETAILED DESCRIPTION OF THE PREFERRED EXAMPLE

The technical feature of the present invention will be described in more detail, accompanied with the following Examples.

Preparation of an Amorphous Divalent Metal Salt

Example 1

Calcium Lactate Gluconate (CLG)

Preparation of CLG 27.0 g of lactic acid (MW=90.1 g/mol), and 35.6 g of gluconolactone (MW=178.0 g/mol) were added into 100 mL deionized water respectively, followed by mixing to prepare a solution. Then, 14.0 g of CaO (MW=56.1 g/mol) was added into the solution. After mixing and stirring for 1 hour, the solution was filtered, and the filtrate was collected. The filtrate was CLG solution, which has a pH value of 9.8. After drying the filtrate, CLG powder was obtained, which has a water solubility of 35.7~41.0 g/100 ml at 25° C.

X-Ray Diffraction (XRD)

Figure 1:
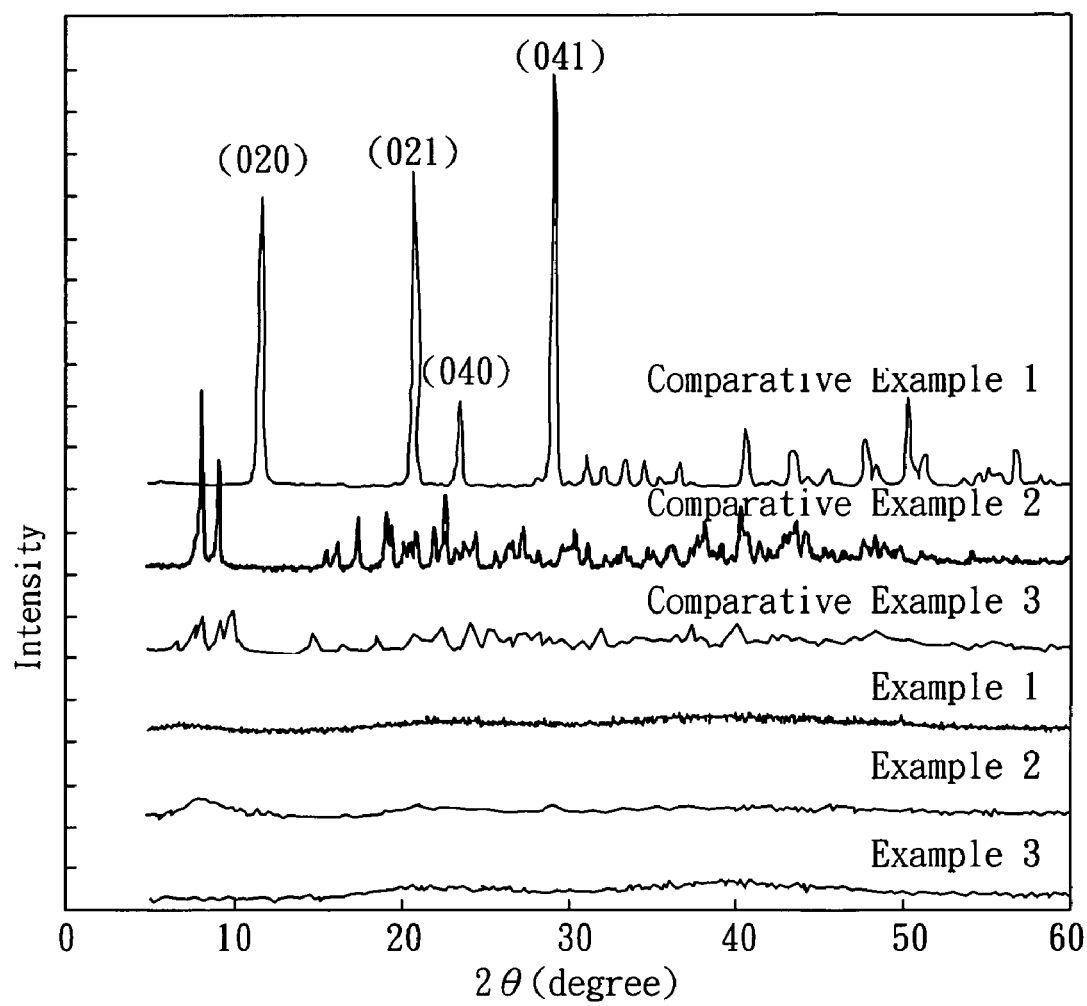
FIG. 1 is an X-ray diffraction diagram of the divalent metal salt prepared in accordance with Comparative Example 1 and Examples 1~3 of the present invention.

The crystal form of the CLG powder prepared above is determined by wide-angle x-ray diffraction (XRD). First, 1.00 g of CLG powder was placed in a sample carrier, and the powder filling was pressed by a slide. Then, the sample was placed on an X-ray diffractometer (MaxRC, Rigaku, Japan), and X-ray diffraction was performed by using Kα radiation ($\lambda$=1.541838A) at scan rate of 10°/min and 2θ scanning angle from 5° to 60°. The peaks of X-ray diffraction data were analyzed in accordance with the Joint Committee on Powder Diffraction Standards (JCPDS). As shown in FIG. 1, the analysis result shows that the CLG powder prepared herein has an amorphous structure.

Example 2

Calcium Lactate Sulfate (CLS)

2.45 g of sulfuric acid (MW=98.1 g/mol), and 1.80 g of lactic acid (MW=90.1 g/mol) were added into 50 mL deionized water respectively, followed by mixing to prepare a solution. Then, 2.00 g of CaO (MW=56.1 g/mol) was added into the solution. After mixing and stirring for 1 hour, the solution was filtered, and the filtrate was collected. The filtrate was CLS solution, which has a pH value of 9.7. After drying the filtrates, CLS powder was obtained, which has a water solubility of 4.6~5.0 g/100 ml at 25° C. The crystal of the product was determined by the same process illustrated in Example 1, and the result shows that the CLS powder has an amorphous structure, as shown in FIG. 1.

Example 3

Calcium Sulfate Gluconate (CSG)

2.45 g of sulfuric acid (MW=98.1 g/mol), and 3.92 g of gluconolactone (MW=178.0 g/mol) were added into 50 mL deionized water respectively, followed by mixing to prepare a solution. Then, 2.00 g of CaO (MW=56.1 g/mol) was added into the solution. After mixing and stirring for 1 hour, the solution was filtered, and the filtrate was collected. The filtrate was CSG solution, which has a pH value of 9.3. After drying the filtrate, CSG powder was obtained, which has a water solubility of 30.1~31.7 g/100 ml at 25° C. The crystal of the product was determined by the same process illustrated in Example 1, and the result shows that CSG powder has an amorphous structure, as shown in FIG. 1.

Comparative Example 1

Calcium Sulfate Dehydrate (CSD)

0.1 mole of potassium sulfate (MW=174.3 g/mol), and calcium nitrate (MW=164.1 g/mol) were added into deionized water respectively, followed by mixing completely, and heating to 95° C. by oil-bath. Then, the two solutions were mixed and reacted at a determined temperature. After 2 hours, the mixture was filtrated and washed by glass fiber filters and a funnel with suction. After drying the sample in an oven, a powder was obtained, which has a water solubility of 0.2 g/100 ml at 25° C. The crystal of the product was determined by the same process illustrated in Example 1, and the result shows that 11.64°, 20.75°, 23.41°, and 29.14° peaks were observed in the 2θ scan of XRD, as shown in FIG. 1. These peaks correspond to the crystal face with (0 2 0), (0 2 1), (0 4 0), (0 4 1), which represents the crystal face of CSD.

Comparative Example 2

Calcium Gluconate (CG)

7.84 g of gluconolactone (MW=178.0 g/mol) were added into 50 mL deionized water respectively, followed by mixing to prepare a solution. Then, 2.00 g of CaO (MW=56.1 g/mol) was added into the solution. After mixing and stirring for 1 hour, the solution was filtered, and the filtrate was collected. After drying the filtrate, CG powder was obtained, which has a water solubility of 3.0~4.0 g/100 ml at 25° C. The crystal of the product was determined by the same process illustrated in Example 1, and the result shows that CG powder has a crystalline structure, as shown in FIG. 1.

Comparative Example 3

Calcium Lactate (CL)

3.60 g of lactic acid (MW=90.1 g/mol) were added into 50 mL deionized water respectively, followed by mixing to prepare a solution. Then, 2.00 g of CaO (MW=56.1 g/mol) was added into the solution. After mixing and stirring for 1 hour, the solution was filtered, and the filtrate was collected. After drying the filtrate, CL powder was obtained, which has a water solubility of 7.0~8.9 g/100 ml at 25° C. The crystal of the product was determined by the same process illustrated in Example 1, and the result shows that CL powder has a crystalline structure, as shown in FIG. 1.

FIG. 1 presents the XRD 2θ-scan and for calcium compounds of calcium gluconate (CG), calcium lactate (CL), and CLG powders. Unlike the revealed amorphous characteristics of the CLG powder, both CG and CL show several sharp peaks in XRD analysis indicating their crystalline properties. The measured solubility for CG, CL, and CLG suggests CLG is an amorphous powder and its solubility is higher than the individual components of CG or CL.

The following Table 1 shows the solubility and the crystal property of the divalent metal salt prepared according to Examples 1~3 and Comparative Example 1~3.

TABLE 1

|  | Example 1 | Example 2 | Example 3 | Comparative Example 1 | Comparative Example 2 | Comparative Example 3 |
| --- | --- | --- | --- | --- | --- | --- |
| Powder | Calcium lactate gluconate | Calcium lactate sulfate | Calcium sulfate gluconate | Calcium sulfate dehydrate | Calcium gluconate | Calcium lactate |

TABLE 1-continued

|  | Example 1 | Example 2 | Example 3 | Comparative Example 1 | Comparative Example 2 | Comparative Example 3 |
|---|---|---|---|---|---|---|
| Solubility (g/100 ml) | 35.7~41.0 | 4.6~5.0 | 30.1~31.7 | 0.2 | 3.0~4.0 | 7.0~8.9 |
| Crystal form | Amorphous | Amorphous | Amorphous | Crystalline | Crystalline | Crystalline |

The Influence of the Amorphous Divalent Metal Salt on the Setting Time of Portland Cement

Example 4

First, the amorphous divalent metal salt prepared according to Example 1 was formulated into a CLG solution at a concentration of 20 wt %. Then, the CLG solution was mixed with Portland cement powder with the L/P ratio of 1:4 by weight.

Test on Setting Time

After Portland cement was mixed with water, the hydration reaction was started immediately. The setting time of Portland cement was detected in accordance with international standard ISO 1566. "Initial setting time" as the term used herein is the time after which a 1 mm diameter pin with a load of 300 g can be inserted less than 1 mm deep into the sample surface. "Final setting time", the term used herein is defined as the time when the pin cannot be inserted into the sample surface.

Example 5

The methods for preparing and testing of the present Example are the same as those illustrated in Example 4, except that 20 wt % of the CLG solution is substituted with 4 wt % of CLS solution prepared with the CLS powder of Example 2.

Example 6

The methods for preparing and testing of the present Example are the same as those illustrated in Example 4, except that 20 wt % of the CLG solution is substituted with 20 wt % of CSG solution prepared with the CSG powder of Example 3.

Comparative Example 4

The methods for preparing and testing of the present comparative Example are the same as those illustrated in Example 4, except that 20 wt % of the CLG solution is substituted with deionized water.

Comparative Example 5

The methods for preparing and testing of the present comparative Example are the same as those illustrated in Example 4, except that 20 wt % of the CLG solution is substituted with 10 wt % of CaCl$_2$ solution.

The following Table 2 shows the setting time of Portland cement according with Examples 4~6 and Comparative Examples 4~5.

TABLE 2

|  | Example 4 | Example 5 | Example 6 | Comparative Example 4 | Comparative Example 5 |
|---|---|---|---|---|---|
| Solution | CLG | CLS | CSG | Water | CaCl$_2$ |
| Concentration (wt %) | 20 | 4 | 20 | — | 10 |
| Initial setting time (min) | 15 | 140 | 10 | 145 | 35 |

Dental Material for Repairing Tooth Cavities

Example 7

2.0 g of beta-tricalcium phosphate (β-TCP), and 7.5 g of Portland cement were placed in 50 mL a mill pot, followed by grinding with a ball mill for 10 min. Then, the amorphous divalent metal salt prepared according to Example 1 was formulated into a CLG solution at a concentration of 23.1 wt %, followed by mixing with Portland cement powder at the L/P ratio of 1:4 by weight. The initial setting time was measured according with the procedure illustrated in Example 4.

Evaluation of Handling Property

The handling property of the dental material for repairing tooth cavities is considered "excellent", "good", "bad", and "very bad", depending upon a blending test devised by 3 dentists and 6 students of dental programs.

Example 8

The methods for preparing and testing of the present Example are the same as those illustrated in Example 7, except that 2.0 g of β-TCP is substituted with 2.0 g of ACP.

Example 9

The methods for preparing and testing of the present Example are the same as those illustrated in Example 7, except that 2.0 g of β-TCP is substituted with 0.5 g of CSD.

The following Table 3 shows the setting time of the dental material for repairing tooth cavities according to Examples 7~9.

TABLE 3

|  | Example 7 | Example 8 | Example 9 |
|---|---|---|---|
| Portland cement (g) | 7.5 | 7.5 | 8.0 |
| β-TCP (g) | 2.0 | — | — |
| ACP (g) | — | 2.0 | — |
| Gypsum (g) | 0.5 | 0.5 | 20 |
| Initial setting time (min) | 20 | 17 | 30~35 |
| Final setting time (min) | 35 | 40 | >60 |
| Handling property | Excellent | Good | Bad (powder) |

Dental Material for Root Canal Filling

Example 10

2.0 g of bismuth oxide, 0.5 g of $CaSO_4$, and 7.5 g of Portland cement were placed in a 50 mL mill pot, followed by grinding with a ball mill for 10 min. Then, the amorphous divalent metal salt prepared according to Example 1 was formulated into a CLG solution at a concentration of 4.8 wt %, followed by mixing with Portland cement powder at the L/P ratio of 1:4 by weight. The initial setting time was measured according to the procedure illustrated in Example 4. The test result shows that the initial setting time of the dental material of the present Example is 120 min.

Example 11

The methods for preparing and testing of the present Example are the same as those illustrated in Example 7, except that 4.8 wt % of CLG solution is substituted with 9.1 wt % of the CLG solution. The test result shows that the initial setting time of the dental material of the present Example is 120 min.

Example 12

The methods for preparing and testing of the present Example are the same as those illustrated in Example 7, except that 4.8 wt % of the CLG solution is substituted with 13.0 wt % of a CLG solution. The test results show that the initial setting time of the dental material of the present Example is 120 min.

Example 13

The methods for preparing and testing of the present Example are the same as those illustrated in Example 7, except that 4.8 wt % of the CLG solution is substituted with 16.7 wt % of a CLG solution. The test results show that the initial setting time of the dental material of the present Example is 90 min.

Example 14

The methods for preparing and testing of the present Example are the same as those illustrated in Example 7, except that 4.8 wt % of the CLG solution is substituted with 20.0 wt % of a CLG solution. The test result shows that the initial setting time of the dental material of the present Example is 90 min.

Example 15

The methods for preparing and testing of the present Example are the same as those illustrated in Example 7, except that 4.8 wt % of the CLG solution is substituted with 23.1 wt % of a CLG solution. The test results show that the initial setting time of the dental material of the present Example is 30 min.

Figure 2:
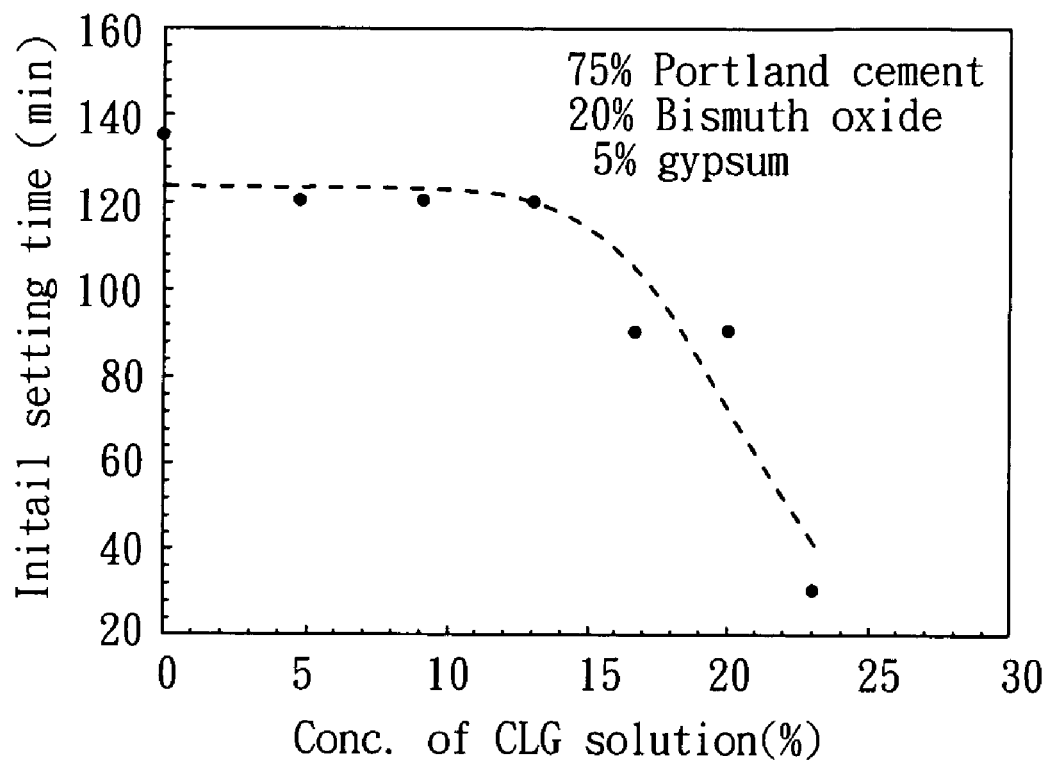
FIG. 2 is a graph illustrating the relation between the concentration of the CLG solution and the initial setting time of the present invention.

FIG. 2 is a graph illustrating the relation between the concentration of the CLG solution and the initial setting time.

Example 16

2.0 g of bismuth oxide, 0.5 g of CSD, and 7.5 g of Portland cement were placed in a 50 mL mill pot, followed by grinding with a ball mill for 10 min. Then, the amorphous divalent metal salt prepared according to Example 1 was formulated into a CLG solution at a concentration of 23.1 wt %, followed by mixing with Portland cement powder at the L/P ratio of 1:2 by weight. The initial setting time and the final setting time were measured according to the procedure illustrated in Example 4.

Example 17

The methods for preparing and testing of the present Example are the same as those illustrated in Example 16, except that the ratio of the CLG solution to Portland cement is 1:3.

Example 18

The methods for preparing and testing of the present Example are the same as those illustrated in Example 16, except that the ratio of the CLG solution to Portland cement is 1:4.

Example 19

The methods for preparing and testing of the present Example are the same as those illustrated in Example 16, except that the ratio of the CLG solution to Portland cement is 1:4.5.

Example 20

The methods for preparing and testing of the present Example are the same as those illustrated in Example 16, except that the ratio of the CLG solution to Portland cement is 1:5.

The following Table 4 shows the setting time of the dental material for root canal filling corresponding to the liquid-to-powder ratio according to Examples 16~20.

TABLE 4

| | Example 16 | Example 17 | Example 18 | Example 19 | Example 20 |
|---|---|---|---|---|---|
| L/P ratio | 1:2 | 1:3 | 1:4 | 1:4.5 | 1:5 |
| Initial setting time (min) | 425 | 40 | 25 | 20 | Cannot be handled |
| Final setting time (min) | 1,045 | 430 | 75 | 60 | Cannot be handled |

Comparative Example 6

The methods for preparing and testing of the present comparative Example are the same as those illustrated in Example 16, except that the CLG solution is substituted with deionized water.

Comparative Example 7

The methods for preparing and testing of the present comparative Example are the same as those illustrated in Example 17, except that the CLG solution is substituted with deionized water.

Comparative Example 8

The methods for preparing and testing of the present comparative Example are the same as those illustrated in Example 18, except that the CLG solution is substituted with deionized water.

Comparative Example 9

The methods for preparing and testing of the present comparative Example are the same as those illustrated in Example 19, except that the CLG solution is substituted with deionized water.

Comparative Example 10

The methods for preparing and testing of the present comparative Example are the same as those illustrated in Example 20, except that the CLG solution is substituted with deionized water.

The following Table 5 shows the setting time of the dental material for root canal filling corresponding to the liquid-to-powder ratio according to Examples 4~8.

TABLE 5

|  | Comparative Example 6 | Comparative Example 7 | Comparative Example 8 | Comparative Example 9 | Comparative Example 10 |
|---|---|---|---|---|---|
| L/P ratio | 1:2 | 1:3 | 1:4 | 1:4.5 | 1:5 |
| Initial setting time (min) | 540 | 225 | 145 | Cannot be handled | Cannot be handled |
| Final setting time (min) | 1,385 | 825 | 215 | Cannot be handled | Cannot be handled |

Example 21

2.0 g of bismuth oxide, 0.5 g of CSD, and 7.5 g of Portland cement were placed in a 50 ml mill pot, followed by grinding with a ball mill for 10 min. Then, the amorphous divalent metal salt prepared according to Example 1 was formulated into a CLG solution at a concentration of 23.1 wt %, followed by mixing with Portland cement powder at the L/P ratio of 1:4 by weight. The initial setting time and the final setting time were measured according to the procedure illustrated in Example 4; and the handling property was evaluated according with the method illustrated in Example 7. The test results show that the initial setting time is 15 min, the final setting time is 30 min, and the handling property is excellent.

Comparative Example 11

The methods for preparing and testing of the present comparative Example are the same as those illustrated in Example 21, except that the CLG solution is substituted with deionized water. The test results shows that the initial setting time is 150 min, the final setting time is 220 min, and the handling property is very bad.

Comparative Example 12

The methods for preparing and testing of the present comparative Example are the same as those illustrated in Example 21, except that the CLG solution is substituted with 10 wt % of $CaCl_{2(aq)}$. The test results show that the initial setting time is 30 min, the final setting time is 60 min, and the handling property is bad.

Example 22

In the present Example, the powder composition is white MTA (WMTA) available from ProRoot®, Dentsply Co., and the amorphous divalent metal salt prepared according to Example 1 was formulated into a CLG solution at a concentration of 23.1 wt %. Then, the white MTA was mixed with the CLG solution at the L/P ratio of 1:4 by weight. The initial setting time and the final setting time were measured according to the procedure illustrated in Example 4; and the handling property was evaluated according with the method illustrated in Example 7. The test results show that the initial setting time is 10 min, the final setting time is 20 min, and the handling property is excellent.

Comparative Example 13

The methods for preparing and testing of the present comparative Example are the same as those illustrated in Example 22, except that the CLG solution is substituted with deionized water. The test results show that the initial setting time is 150 min, the final setting time is 200 min, and the handling property is very bad.

Comparative Example 14

The methods for preparing and testing of the present comparative Example are the same as those illustrated in Example 21, except that the CLG solution is substituted with 10 wt % of $CaCl_2$ solution. The test results show that the initial setting time is 20 min, the final setting time is 45 min, and the handling property is bad.

The following Table 6 shows the setting time of the dental material for root canal filling according to Examples 21~22, and Comparative Examples 9~12.

TABLE 6

|  | Example 21 | Comparative Example 11 | Comparative Example 12 | Example 22 | Comparative Example 13 | Comparative Example 14 |
|---|---|---|---|---|---|---|
| Powder composition | Bismuth oxide (2.0 g) $CaSO_4$ (0.5 g) Portland cement (7.5 g) | | | White MTA | | |
| Solution of divalent metal salt | 23.1 wt % $CLG_{(aq)}$ | Water | 10 wt % $CaCl_{2(aq)}$ | 23.1 wt % $CLG_{(aq)}$ | Water | 10 wt % $CaCl_{2(aq)}$ |
| Initial setting time (min) | 15 | 150 | 30 | 10 | 150 | 20 |

TABLE 6-continued

|  | Example 21 | Comparative Example 11 | Comparative Example 12 | Example 22 | Comparative Example 13 | Comparative Example 14 |
|---|---|---|---|---|---|---|
| Final setting time (min) | 30 | 220 | 60 | 20 | 200 | 45 |
| Handling property | Excellent | Very bad (powder) | Bad | Excellent | Very bad (powder) | Bad |

Example 23

The powder composition of the dental material for root canal filling, which comprises 7.5 parts of Portland cement, 2.0 parts of bismuth oxide, and 0.5 parts of $CaSO_4$, was mixed with water at the L/P ratio of 1:4 by weight. Then, the mixture was shaped into a round tablet with a diameter of 10 mm and a thickness of 1 mm. Radiopacity test and Whiteness test were performed to evaluate the influence of radiopaque substance on X-ray radiopacity and the appearance of tooth, when bismuth oxide was substituted with bismuth subcarbonate.

Radiopacity Test

After the powder composition had been mixed with water, the mixture was shaped into a round tablet with a diameter of 10 mm and a thickness of 1 mm, and the radiopacity of samples was evaluated by comparison to that of aluminum step wedge with thickness of 2~16 mm, according to ISO Standard 6876:2001. First, an X-ray digital camera operating at 50 kVp, 10 mA, 18 pulses/s, and focus-film distance of 33.5 cm, was used for taking the radiographs of samples and the aluminum step wedge. Then, the grayscale radiographs of the samples were compared with those of the aluminum step wedge to obtain the radiopacity of the samples, which was equivalent to a particular thickness of aluminum, measured in millimeters. Herein, the unit of the radiopacity is presented in millimeters of aluminum (mm Al).

Whiteness Test

After the dental composition for root canals had been mixed and set, the sample was shaped into a round tablet with a diameter of 10 mm and a thickness of 1 mm. Then, the sample was measured by a color meter, and the color of the sample was quantified by CIE L*, a*, and b* color coordinates. The test was performed 5 times to obtain an averaged value. Herein, L* represents the lightness, and L*=100 means white or transparent. a* and b* represent the color, wherein +a represents red, −a represents green, +b represents yellow, and −b represents blue.

Example 24

The methods for preparing and testing of the present Example are the same as those illustrated in Example 23, except that bismuth oxide is replaced by bismuth subcarbonate.

Test Results of Radiopacity and Whiteness

The test results show that the radiopacity of the dental materials for root canal filling containing bismuth subcarbonate (Example 24) and bismuth oxide (Example 23) is 6 and 7 mm Al, respectively. According to the standard of ISO 6876: 2001, the radiopacity of the dental materials for root canal filling has to be greater than 2 mm Al. As to the whiteness, L and −a of the dental material containing bismuth subcarbonate (Example 24) are 97.33 and −1.23, respectively. However, L and −a of the dental material containing bismuth oxide (Example 23) are 94.04 and −5.75, respectively. Hence, the color of the dental material containing bismuth subcarbonate is whiter and less green than that of the dental material containing bismuth oxide. Therefore, it is possible to reduce the influence on the appearance of the repaired tooth by using bismuth subcarbonate.

The following Table 7 shows the radiopacity and whiteness of the dental material for root canal filling according to Examples 23~24.

TABLE 7

|  |  | Example 23 | Example 24 |
|---|---|---|---|
| Portland cement (g) |  | 7.5 | 7.5 |
| Bismuth oxide (g) |  | 2.0 | — |
| Bismuth carbonate (g) |  | — | 2.0 |
| Gypsum $CaSO_4$ (g) |  | 0.5 | 0.5 |
| Radiopacity (mm Al) |  | 7 | 6 |
| CIE Lab | L | 94.04 | 97.33 |
|  | a | −5.75 | −1.23 |
|  | b | 14.87 | 3.31 |

L: brightness;
a: green;
b: yellow

<Test Result>

FIG. 1 is an X-ray diffraction diagram showing different kinds of divalent metal salt. As shown in FIG. 1, the metal salt form with two organic and/or inorganic acid anions. They are independently and different. The crystal form is amorphous. Further, FIG. 2 is a graph illustrating the relation between the concentration of the CLG solution and the initial setting time. As shown in FIG. 2, the initial setting time of the dental material is about 135 min, when the CLG solution is unused. As the concentration of the CLG solution is increased, the initial setting time of the dental material is shortened.

In order to realize the character of the amorphous divalent metal salt of the present invention and its application to the dental field, Table 1 shows the relation between the solubility and the crystal property of the divalent metal salts, and Table 2 shows the influence of the divalent metal salts on the setting time of Portland cement. As shown in Table 1, the divalent metal salt, which is formed by a divalent metal ion and two different organic and/or inorganic acid anions, is amorphous and with high solubility. As shown in Table 2, the solution of amorphous divalent metal salt can enhance the setting time of Portland cement.

Table 3 shows the setting times of different dental materials for repairing tooth cavities. The test results show that adding calcium phosphate bone substitute can also enhance the setting time of Portland cement.

Table 4 and 5 show the setting time of the root canal materials with different L/P ratios; the CLG solution and deionized water were used as liquid, respectively. The test results show that when the powder composition is mixed with a liquid at the L/P ratio of 1:2~1:4.5, the setting time of the dental composition by using the CLG solution as a liquid is shorter than that by using deionized water. Table 6 shows the influence of different solutions on the setting time and handling property of the dental material. The test result shows that when the powder composition is mixed with liquid at the L/P ratio of 1:4, the setting time and the handling property of the dental material by using the CLG solution are better than those by using deionized water or $CaCl_{2(aq)}$. Table 7 shows the radiopacity and whiteness after the dental materials for the root canals containing different radiopaque substance are set. The test result shows that the radiopacities of the dental materials containing bismuth subcarbonate or bismuth oxide all meet the standard of ISO 6876:2001. However, the dental material containing bismuth subcarbonate shows greater whiteness and less green than that containing bismuth oxide. Hence, the appearance of repaired tooth color can be improved by use of bismuth subcarbonate as a radiopaque substance.

In conclusion, the amorphous divalent metal salt of the present invention has excellent solubility, and can provide $Ca^{2+}$ to enhance the setting reaction of Portland cement. Also, when the CLG is saturated, the CLG educts can increase the viscosity of Portland cement, so the handling property can be facilitated. Furthermore, the color of bismuth subcarbonate is lighter than common bismuth oxide, so the problem of deep color of repaired tooth can be improved. Therefore, the repaired tooth appears natural when bismuth subcarbonate is used as a radiopaque substance.

Although the present invention has been explained in relation to its preferred Example, it is to be understood that many other possible modifications and variations can be made without departing from the scope of the invention as hereinafter claimed.

What is claimed is:

1. A dental material for repairing tooth cavities, comprising:
   a powder composition, comprising a Portland cement, and a calcium phosphate bone substitute; and
   a solution of an amorphous divalent metal salt, represented by the following formulas (I), (II), or (III):

$$M^{2+}A_x^- B_{2-x}^- \quad (I)$$

$$M^{2+}A_{\frac{y}{2}}^- C_{\frac{(4-y)}{4}}^{2-} \quad (II)$$

$$M^{2+}A_{\frac{z}{3}}^- D_{\frac{(6-z)}{9}}^{3-} \quad (III)$$

wherein, $M^{2+}$ is a metal ion, each $A^-$, $B^-$, $C^{2-}$, $D^{3-}$ independently is a $C_1 \sim C_{15}$ organic, or an inorganic acid anion, $A^-$, $B^-$, $C^{2-}$, $D^{3-}$ are different from each other; $0<x<2$, $0<y<4$, and $0<z<6$, and the calcium phosphate bone substitute is β-tricalcium phosphate, or amorphous calcium phosphate.

2. The dental material of claim 1, wherein the Portland cement is type I Portland cement.

3. The dental material of claim 1, wherein $M^{2+}$ is selected from the group consisting of $Be^{2+}$, $Mg^{2+}$, $Ca^{2+}$, $Sr^{2+}$, and $Ba^{2+}$.

4. The dental material of claim 1, wherein the inorganic acid anion is selected from the group consisting of nitrate, sulfate, chloride, and phosphate.

5. The dental material of claim 1, wherein the organic acid anion is selected from the group consisting of gluconate, lactate, pyruvate, glycolate, chloractate, dichloroacetate, trichloroacetate, cyanoacetate, tartrate, succinate, glutarate, maleate, fumarate, malonate, citraconate, ortho-phthalate, meta-phthalate, para-phthalic, citrate, 1,2,3-propanetricarboxylate, trimellitate, and 1,3,5-pentanetricarboxylate.

6. The dental material as claimed of claim 1, wherein $A^-$ is lactate, $B^-$ is gluconate, and $C^{2-}$ is sulfate.

7. The dental material of claim 1, wherein the amorphous divalent metal salt is calcium lactate gluconate (CLG), calcium lactate sulfate (CLS), or calcium sulfate gluconate (CSG).

8. The dental material of claim 1, wherein the solution of the amorphous divalent metal salt is at a concentration of between 5% and 30% by weight, and the liquid-to-powder ratio of the solution of the amorphous divalent metal salt to the powder composition is between 1:2 and 1:5.

9. A dental material for root canal filling, comprising:
   a powder composition, comprising a Portland cement, and a radiopaque substance; and
   a solution of an amorphous divalent metal salt, represented by the following formulas (I), (II), or (III):

$$M^{2+}A_x^- B_{2-x}^- \quad (I)$$

$$M^{2+}A_{\frac{y}{2}}^- C_{\frac{(4-y)}{4}}^{2-} \quad (II)$$

$$M^{2+}A_{\frac{z}{3}}^- D_{\frac{(6-z)}{9}}^{3-} \quad (III)$$

wherein, $M^{2+}$ is a metal ion, each $A^-$, $B^-$, $C^{2-}$, $D^{3-}$ independently is a $C_1 \sim C_{15}$ organic, or an inorganic acid anion, $A^-$, $B^-$, $C^{2-}$, $D^{3-}$ are different from each other; $0<x<2$, $0<y<4$, and $0<z<6$, and the radiopaque substance is bismuth subcarbonate, or bismuth oxide.

10. The dental material of claim 9, wherein the Portland cement is type I Portland cement.

11. The dental material of claim 9, wherein $M^{2+}$ is selected from the group consisting of $Be^{2+}$, $Mg^{2+}$, $Ca^{2+}$, $Sr^{2+}$, and $Ba^{2+}$.

12. The dental material of claim 9, wherein the inorganic acid anion is selected from the group consisting of nitrate, sulfate, chloride, and phosphate.

13. The dental material of claim 9, wherein the organic anion is selected from the group consisting of gluconate, lactate, pyruvate, glycolate, chloractate, dichloroacetate, trichloroacetate, cyanoacetate, tartrate, succinate, glutarate, maleate, fumarate, malonate, citraconate, ortho-phthalate, meta-phthalate, para-phthalic, citrate, 1,2,3-propanetricarboxylate, trimellitate, and 1,3,5-pentanetricarboxylate.

14. The dental material of claim 9, wherein is lactate, $B^-$ is gluconate, and $C^{2-}$ is sulfate.

15. The dental material of claim 9, wherein the amorphous divalent metal salt is calcium lactate gluconate (CLG), calcium lactate sulfate (CLS), or calcium sulfate gluconate (CSG).

16. The dental material of claim 9, wherein the solution of the amorphous divalent metal salt is at a concentration of between 5% and 30% by weight, and the liquid-to-powder ratio of the solution of the amorphous divalent metal salt to the powder composition is between 1:2 and 1:5.

* * * * *

UNITED STATES PATENT AND TRADEMARK OFFICE
CERTIFICATE OF CORRECTION

PATENT NO. : 8,298,328 B2  
APPLICATION NO. : 12/591764  
DATED : October 30, 2012  
INVENTOR(S) : Jen-Chang Yang et al.

It is certified that error appears in the above-identified patent and that said Letters Patent is hereby corrected as shown below:

Title Page, Item (75)

"Inventors: Jeng-Chang Yang, Taipei (TW); Pei-Ying Lee, Taipei (TW); Dian-Yu Ji, Taipei (TW); Nai-Chia Teng, Taipei (TW); Sung-Chih Hsieh, Sindian (TW); Sheng-Yang Lee, Taipei (TW)"

should read:

-- Inventors: Jen-Chang Yang, Taipei (TW); Pei-Ying Lee, Taipei (TW); Dian-Yu Ji, Taipei (TW); Nai-Chia Teng, Taipei (TW); Sung-Chih Hsieh, Sindian (TW); Sheng-Yang Lee, Taipei (TW) --

Signed and Sealed this  
Fifth Day of February, 2013

Teresa Stanek Rea  
*Acting Director of the United States Patent and Trademark Office*